United States Patent [19]

Engel et al.

[11] 4,323,715
[45] Apr. 6, 1982

[54] PREPARATION OF MONO-TERTIARY BUTYLHYDROQUINONE

[75] Inventors: Dusan J. Engel, Des Plaines; Thomas P. Malloy, Lake Zurich, both of Ill.

[73] Assignee: UOP Inc., Des Plaines, Ill.

[21] Appl. No.: 208,954

[22] Filed: Nov. 20, 1980

[51] Int. Cl.³ ...................... C07C 37/11; C07C 39/08
[52] U.S. Cl. ................................. 568/766; 568/789; 568/794
[58] Field of Search .............. 568/766, 790, 794, 789, 568/785, 784

[56] References Cited

U.S. PATENT DOCUMENTS

| | | | |
|---|---|---|---|
| 3,290,389 | 12/1966 | Hahn | 568/794 |
| 3,670,030 | 6/1972 | Sparks | 568/789 |
| 4,108,909 | 8/1978 | Leach et al. | 568/794 |
| 4,232,176 | 11/1980 | Adigamov et al. | 568/789 |

FOREIGN PATENT DOCUMENTS 210181  3/1968  U.S.S.R. .............................. 568/794

Primary Examiner—Werren B. Lone
Attorney, Agent, or Firm—James R. Hoatson, Jr.; Raymond H. Nelson; William H. Page II

[57] ABSTRACT

Mono-tertiary butylhydroquinone may be prepared in a continuous method of operation by reacting hydroquinone with isobutylene in the presence of an acidic alumina catalyst. The alkylation is effected in a reaction medium which comprises an ether, and particularly a polyether such as the dimethyl ether of triethylene glycol.

9 Claims, No Drawings

PREPARATION OF MONO-TERTIARY BUTYLHYDROQUINONE

BACKGROUND OF THE INVENTION

Mono-tertiary butylhydroquinone (MTBHQ) is a compound which has been shown to possess excellent antioxidant properties with a concomitant low toxicity. The compound is utilized as an antioxidant in the food industry or as an intermediate in the preparation of other chemicals. MTBHQ is used as an antioxidant for fat, lards, oils and fat-containing food, either by incorporation into the food stuff itself or by being incorporated in the material which is used to encase or wrap the particular food stuff. In addition, the use of this compound is likely to increase in the future due to the low toxicity and higher solubility which the process relates to butylated hydroxyanisole (BHA) which heretofor has been widely used as an antioxidant in foods.

Other possible uses for this compound could include the use as a stabilizer in irradiated polypropylene, as an inhibitor for unsaturated polyester, as a stabilizer for polyethylene glycol or other polymerizable systems and to improve the color stability of gasoline antioxidants.

One method of preparing this compound is to alkylate hydroquinone with an alkylating agent such as the olefin, isobutylene, or the alcohol, t-butyl alcohol, said reaction being effected in the presence of an acidic catalyst and in a reaction medium comprising a hydrocarbon solvent. However, certain deficiencies are present in this process which renders said process difficult to effect at an acceptable economical return. For example, when utilizing hydrocarbon solvent such as xylene for the reaction medium, an elaborate work-up section is required due to the fact that the presence of xylene in the reaction product requires azeotropic distillation with water followed by a number of crystallization steps to improve the purity of the final product. In addition, an object of the process is to obtain the mono-alkylated product in as great a yeild as possible. Inasmuch as the amount of di-alkylated product which is formed during the reaction is present in an inordinant amount, it is necessary to separate the two compounds in order to provide an effective antioxidant compound. The separation step which may be necessary therefore entails an additional operating procedure as well as requiring additional equipment, all of which adds to the overall cost of the process, thereby reducing the return on the finished product.

As will hereinafter be shown in greater detail, it has now been discovered that by effecting the alkylation reaction in a reaction medium of a certain type, it is possible to obtain a greater amount of mono-alkylated product while concomitantly increasing the selectivity to the desired product.

DETAILED DESCRIPTION OF THE INVENTION

This invention relates to a process for preparing tertiary butylhydroquinone. More particularly the invention is concerned with an improvement in a process for the alkylation of hydroquinone with an alkylating agent whereby a greater amount of mono-alkylated product is produced.

As hereinbefore set forth, mono-tertiary butylhydroquinone is finding an increased use in the food industry as an additive to food stuffs to act as an antioxidant and thus prevent the deterioration, or spoilation of said food stuffs. The mono-tertiary butylhydroquinone possesses greater antioxidant properties than does the corresponding di-tertiary butylhydroquinone, and therefore when preparing the antioxidant via the alkylation reaction, it is preferred that a relatively greater amount of mono- product be obtained in relation to the di- product.

It is therefore an object of this invention to provide a process for the preparation of mono-tertiary butylhydroquinone.

A further object of this invention is to provide an improvement in the process which involves the alkylation of hydroquinone with an alkylating agent whereby improved yields of the mono-alkylated product are obtained.

In one aspect, an embodiment of the invention resides in a process for the preparation of tertiary butylhydroquinone which comprises alkylating hydroquinone with isobutylene or t-butyl alcohol in the presence of an alkylation catalyst comprising an acidic alumina at alkylation conditions in a reaction medium comprising an ether, and recovering the tertiary butylhydroquinone.

A specific embodiment of this invention is found in the process for the preparation of tertiary butylhydroquinone which comprises alkylating hydroquinone with isobutylene in the presence of an alkylation catalyst comprising a fluorided alumina containing 1% by weight of fluorine at a temperature in the range of from about 100° to about 250° C. and a pressure in the range of from about 50 to about 1500 psig in a reaction medium comprising the dimethyl ether of triethylene glycol, and recovering the resultant tertiary butylhydroquinone.

Other objects and embodiments will be found in the following further detailed description of the invention.

As hereinbefore set forth, the present invention is concerned with a process for preparing tertiary butylhydroquinone and more specifically to a process for increasing the yield of the mono-alkylated product with respect to the di-alkylated product. By effecting the reaction in the presence of a certain reaction medium of the type hereinafter set forth in greater detail, it has now been discovered that the desired result may be attained in a relatively simple manner.

The alkylation process of the present invention in which hydroquinone is reacted with an alkylating agent comprising, in the preferred embodiment of the invention, isobutylene is effected under alkylation conditions which include temperatures in the range of from about 50° to about 250° C. and pressures which may range from about 50 up to about 1500 or more pounds per square inch gauge (psig). The superatmospheric pressures are afforded by the introduction of a substantially inert gas such as nitrogen, helium, argon, etc. into the reaction mixture. In addition, another operating condition will include residence times which may range from about 0.5 up to about 10 hours or more in duration, the particular residence time which is employed being dependent upon the various reaction parameters such as temperature and pressure which are employed in the reaction. In addition, it is also contemplated within the scope of this invention that various liquid hourly space velocities (LHSV) in the range of from about 0.1 to about 2 or more may also be employed. While, as hereinbefore set forth, the preferred alkylating agent comprises isobutylene, it is also contemplated within the scope of this invention that t-butyl alcohol may also be used, although not necessarily with equivalent results.

The catalyst which is utilized to effect the desired reaction will comprise an acidic alkylation catalyst, and preferably an acidic alumina. In the preferred embodiment of the invention, the acidic alumina which is employed will comprise a fluorided alumina in which the fluorine is present in an amount of from about 1% to about 5% fluorine by weight of the alumina. However, it is also contemplated that an alumina such as gamma alumina, alpha alumina, etc. which has been treated with other acids such as hydrochloric acid, hydrobromic acid, etc. may also be used, although not necessarily with equivalent results.

The reaction medium which is employed in the process of the present invention and which will permit the recovery of a relatively greater amount of mono-alkylated product with respect to the di-alkylated product will comprise an oxygenated organic compound and preferably an ether. By utilizing certain ether compounds, it is possible to utilize both a batch-type operation and a continuous-type operation to prepare the desired product. Certain ethers of the type hereinafter set forth in greater detail may be utilized with solvents for the reaction inasmuch as the ethers are relatively unreactive and possess the ability to dissolve the hydroquinone reactant. Specific examples of these ethers will include tetrahydrofuran as well as polyethers such as cyclic ethers as exemplified by 1,3-dioxane, 1,4-dioxane, etc; aliphatic mono-ethers such as the dimethyl ether of diethylene glycol, the dimethyl ether of triethylene glycol, the diethyl ether of diethylene glycol, the diethyl ether of triethylene glycol, etc.

Due to the ability of the ethers which are used in a reaction medium to act as a solvent for hydroquinone as well as being relatively unreactive with respect to the catalyst and the reactants, it is possible to effect the processes of this invention in a continuous type of operation. Inasmuch as hydroquinone as well as tertiary butylhydroquinone possess a relatively high melting point, it is virtually impossible to utilize a continuous flow operation due to the problems which would be encountered in pumping and handling. Therefore, the use of a solvent which would permit a continuous type operation has rendered this process commercially attractive to operate. The continuous flow fixed bed type of operation may be effected by placing the acidic alumina catalyst in the reaction apparatus and thereafter passing the liquid feed over the catalyst bed at a predetermined liquid hourly space velocity in the range hereinbefore set forth. The liquid feed comprising isobutylene and the hydroquinone which is dissolved in the ether solvent may be passed over the catalyst bed in either an upward or downward flow. After passage over the catalyst bed, the reactor effluent is continuously withdrawn and subjected to conventional means of separation whereby the tertiary butylhydroquinone which has been formed during the reaction is separated from unreacted starting materials, the latter then being recycled to the reactor zone to form a portion of the feed stock while the former may then be subjected to further separation steps in order to separate the mono-tertiary butylhydroquinone from the di-tertiary butylhydroquinone.

While the preferred method of effecting the process of this invention comprises a continuous type of operation, it is also contemplated within the scope of this invention that the desired product may be prepared in a batch-type operation. When such a type of operation is utilized, the catalyst is placed in an appropriate alkylation reaction vessel. Following this, the hydroquinone, which is dissolved in an appropriate ether, is charged to the vessel along with the alkylating agent. The vessel is then sealed and heated to the desired operating temperature and, if so desired, superatmospheric pressure, the latter being afforded by the introduction of an inert gas such as nitrogen, argon, helium, etc. into the reaction vessel. After allowing the alkylation reaction to proceed for a predetermined period of time, heating is discontinued and the apparatus is allowed to return to room temperature. The reaction mixture is recovered and further cooled by means of an ice bath to a temperature of approximately 10° C. Following this, the reaction product comprising a mixture of mono- and di-tertiary hydroquinone is separated from the solvent, catalyst and reacted starting materials by conventional means; by filtration, centrifugation, etc. and thereafter further separated by conventional means such as dissolution in boiling water followed by filtration, drying, etc. to separate the mono-alkylated product from the di-alkylated product.

The following examples are given for purposes of illustrating the processes of this invention. However, it is to be understood that these examples are given merely for purposes of illustration and that the present invention is not necessarily limited thereto.

EXAMPLE I

A fixed bed reactor was loaded with 52 cc. (30 grams) of an alumina catalyst containing 1% fluorine. The reactor was sealed and purged by treatment with nitrogen and thereafter pressure tested with nitrogen. The feed stock comprising a 20% solution of hydroquinone in the dimethyl ether of triethylene glycol was pumped into the reactor to displace the nitrogen, and after the nitrogen had been displaced, isobutylene was admixed with the feed stock and charged at the bottom of the reactor. The feed stock was introduced into the reactor at a liquid hourly space velocity of 1 and a pressure of 750 psig, while maintaining the temperature of the reactor at 170° C. After passage of the feed stock through the reactor for a period of 10 hours, the effluent was subjected to chromatographic analysis. This analysis determined that there had been a 22% conversion of hydroquinone, a 32% conversion of isobutylene with a 100% mole selectivity to mono-tertiary butylhydroquinone.

When the above experiment was repeated utilizing similar conditions of temperature and pressure but by charging the feed stock to the reactor at a liquid hourly space velocity of 2.0, there was obtained an 11% conversion of hydroquinone and a 33% conversion of isobutylene, the mole selectivity of the product being about 100% mono-tertiary butylhydroquinone and 0% di-tertiary butylhydroquinone.

EXAMPLE II

In this example, the above experiment was repeated by charging the feed stock similar in nature to that hereinbefore set forth to the reactor containing the fluorided alumina catalyst at a liquid hourly space velocity of 1.0 at a pressure of 1000 psig while maintaining the temperature of the reactor at 200° C. Analysis of the product showed that there had been a 38% conversion of the hydroquinone, a 75% conversion of the isobutylene with a mole selectivity of 82% mono-tertiary butylhydroquinone and 4% di-tertiary butylhydroquinone, thus giving a ratio of mono-alkylated product to di-alkylated product of 20:1.

When the above experiment was repeated while charging the feed stock to the reactor at a liquid hourly space velocity of 2.0 for a period of 6 hours, analysis of the product determined that there had been a 24% conversion of the hydroquinone and a 45% conversion of the isobutylene. The mole selectivity of the product consisted of about 94% mono-tertiary butylhydroquinone and 6% di-tertiary butylhydroquinone for a ratio of 16:1 moles of mono-alkylated product per mole of di-alkylated product.

EXAMPLE III

In this example, 52 cc of a catalyst comprising 4.5% fluorine on alumina was placed in a reactor and was also thereafter charged with nitrogen. The feed stock was charged to the reactor to displace the nitrogen and thereafter a mixture of 20% hydroquinone solution in the dimethyl ether of triethylene glycol and isobutylene was charged to the reactor at a liquid hourly space velocity of 1.0 while maintaining a pressure of 750 psig and a temperature of 170° C. After a period of 10 hours, analysis of the product determined that there had been a 31% conversion of the hydroquinone and a 59% conversion of isobutylene. The mole selectivity of the product was 88% mono-tertiary butylhydroquinone and 12% di-tertiary butylhydroquinone for a mole ratio of mono-alkylated product to di-alkylated product of 7.5:1.

EXAMPLE IV

To illustrate the efficiency of operating the process in a continuous type of operation, additional experiments were performed in which the reactor effluent which was obtained from a run was recycled back to the reactor. The reactor was charged with 52 cc of catalyst consisting of alumina containing 1% by weight of fluorine. After treatment of the reactor in a manner similar to that set forth in the above examples, a feed stock comprising a 20% hydroquinone solution in the dimethyl ether of triethylene glycol and isobutylene, said reactants being present in a 1:1 mole ratio, was charged to the reactor at a liquid hourly space velocity of 1.0 for a period of 10 hours while maintaining a pressure of 750 psig and a temperature of 170° C. The reactor effluent which was analyzed by chromatgraphic means showed a 22.0% conversion of hydroquinone and a 32% conversion of isobutylene, with a mole selectivity of 100% mono-tertiary butylhydroquinone and 0% di-tertiary butylhydroquinone. The effluent was then recycled through the reactor with an additional amount of isobutylene to maintain the mole ratio balance at a liquid hourly space velocity of 1.0, a pressure of 1000 psig, and a temperature of 200° C. After passage through the reactor, the effluent was analyzed, the mole selectivity of the product showing 55.6% mono-tertiary butylhydroquinone and 3.7% di-tertiary butylhydroquinone, and having a 44.9% conversion of hydroquinone and a 48.5% conversion of isobutylene. The total hydroquinone conversion in two passages, i.e. one recycle, was therefore 57% and mono/di ratio was 15.

Similarly, the reactor effluent was recycled through the reactor at a liquid hourly space velocity of 2.0 for a period of 6 hours while maintaining operating conditions of 1000 psig and a temperature of 200° C. Analysis determined that there had been a 37.1% conversion of hydroquinone and a 40.7% conversion of isobutylene, the mole selectivity of the product showing 69.3% mono-tertiary butylhydroquinone and 4.2% di-tertiary butylhydroquinone. The total hydroquinone conversion in two passages, i.e. one recycle, was 50.9%, the selectivity to mono-alkylated product was 69%, and a weight ratio of mono-alkylated product to di-alkylated product was 16.5.

We claim as our invention:

1. A process for the preparation of tertiary butylhydroquinone which comprises alkylating hydroquinone with isobutylene or t-butyl alcohol in the presence of an alkylation catalyst comprising an acidic alumina at alkylation conditions in a reaction medium comprising an ether selected from the group consisting of tetrahydrofuran, dioxane, dimethyl ether of diethylene glycol, dimethyl ether of triethylene glycol, diethyl ether of diethylene glycol and diethyl ether of triethylene glycol, and recovering the tertiary butylhydroquinone.

2. The process as set forth in claim 1 in which said alkylation conditions include a temperature in the range of from about 100° to about 250° C., and a pressure in the range of from about 50 to about 1500 psig.

3. The process as set forth in claim 1 in which said acidic alumina comprises a fluorided alumina.

4. The process as set forth in claim 3 in which said fluorided alumina contains from about 1% to about 5% by weight of fluorine.

5. The process as set forth in claim 1 in which said ether is tetrahydrofuran.

6. The process as set forth in claim 1 in which said ether is the dimethyl ether of diethylene glycol.

7. The process as set forth in claim 1 in which said ether is the dimethyl ether of triethylene glycol.

8. The process as set forth in claim 1 in which said ether is dioxane.

9. The process as set forth in claim 1 which the hydroquinone is alkylated with isobutylene.

* * * * *